(12) United States Patent
Triplett et al.

(10) Patent No.: US 7,393,678 B2
(45) Date of Patent: Jul. 1, 2008

(54) KLEBSIELLA PNEUMONIAE INOCULANTS FOR ENHANCING PLANT GROWTH

(75) Inventors: Eric W. Triplett, Middleton, WI (US); Shawn M. Kaeppler, Oregon, WI (US); Marisa K. Chelius, Greeley, CO (US)

(73) Assignee: Wisconsin Alumni Research Foundation, Madison, WI (US)

( * ) Notice: Subject to any disclaimer, the term of this patent is extended or adjusted under 35 U.S.C. 154(b) by 443 days.

(21) Appl. No.: 10/720,459

(22) Filed: Nov. 24, 2003

(65) Prior Publication Data

US 2004/0116291 A1 Jun. 17, 2004

Related U.S. Application Data

(62) Division of application No. 10/005,412, filed on Dec. 3, 2001, now abandoned.

(60) Provisional application No. 60/251,137, filed on Dec. 4, 2000.

(51) Int. Cl.
 C12N 1/20 (2006.01)
 A12N 63/00 (2006.01)
(52) U.S. Cl. .................... 435/252.1; 504/117; 424/93.4
(58) Field of Classification Search .................. None
 See application file for complete search history.

(56) References Cited

U.S. PATENT DOCUMENTS

| | | | |
|---|---|---|---|
| 4,149,869 A | 4/1979 | Lloyd | |
| 4,562,663 A | 1/1986 | Redenbaugh | |
| 4,828,600 A | 5/1989 | McCabe et al. | |
| 4,875,921 A | 10/1989 | Paau | |
| 5,451,241 A | 9/1995 | Cartson et al. | |
| 5,552,138 A | 9/1996 | Handelsman et al. | |
| 2002/0119556 A1* | 8/2002 | Husseneder et al. | 435/252.3 |

FOREIGN PATENT DOCUMENTS

| | | |
|---|---|---|
| EP | 1036492 A1 | 9/2000 |
| WO | WO 98/30100 | 7/1998 |
| WO | WO 98/57543 | 12/1998 |

OTHER PUBLICATIONS

Haahtela K, Tuula T, Nurmiaho-Lassila E and Korhonen T K 1988 Effects of inoculation of Poa pratensis and Triticum aestivum with root-associated, N2-fixing Klebsiella, Enterobacter and Azospirillum. Plant and Soil 106, 239-248.*
Lee et al., Plant and Soil 69, 1982, pp. 391-399.*
G. Hoflich et al., "Growth stimulation of pea after inoculation with associative bacteria." Microbiol Research 149:99-104 (1994).
R. Remus et al., "Colonization behaviour of two enterobacterial strains on cereals." Biology and Fertility of Soils, (Mar. 2000) 30:550-557.
R. Remus et al., "Colonization behaviour-of-two enterobacterial strains on cereals."—Biology and Fertility of Soils, Mar. 2000 vol. 30, pp. 550-557. (Abstract).

V. Arangarasan et al., "Inoculation effects of diazotrophs and phosphobacteria on rice." Indian Journal of Microbiology, (1998) 38:111-112 (Abstract).
Vld, Baldini et al., "Inoculation of rice plants with the endophytic diazotrophs *Herbaspirillum seropedicae* and *Burkholderia* spp." Biology of Fertility and Soils, (2000) 30:485-491.
F. Bastian et al., "Production of indole-3-acetic acid and gibberellins A1 and A3 by *Acetobacter diazotrophicus* and *Herbaspirillum seropedicae* in chemically-defined culture media." Plant Growth Regulation, (Jan. 1998) 24:7-11 (Abstract).
A.K. Goel et al., "Use of biofertilizers: Potential, constrains and future strategies- a review." International Journal of Tropical Agriculture, (Mar.-Dec. 1999) 17:1-18 (Abstract).
F. Bastian et al., "Inoculation with *Acetobacter diazotrophicus* Increase Glucose and Fructose Content in Shoots of *Sorghum bicolor* (L.) Monech" Symbiosis (1999), 27(2), 147-156.
G. Kirchhof et al., "Molecular assay to identify *Acetobacter diazotrophicus* and detect its occurrence in plant tissues", Canadian Journal of Microbiology (1998), 44(1), 12-19.
M. Sevilla et al., "Contributions of the Bacterial Endophyte *Acetobacter diazotrophicus* to Sugarcane Nutrition: A Preliminary Study" Symbiosis, (1998) vol. 25, No. 1-3, pp. 181-191.
E. Karpati et al., "Study of wheat and rice cultivas in association with nitrogen-fixing bacteria." Novenytermeles, (2000) 49:233-244 (Abstract).
B. Rethati et al., "Characterization of Hungarian rice cultivars in nitrogen fixing associations with bacteria." Cereal Research Communications, (2000) 28:9-16 (Abstract).
P.J. Riggs et al., "Enhanced maize productivity by inoculation with diazotrophic bacteria." Australian Journal of Plant Physiology, (2001) 28:829-836 (Abstract).
E. Triplett et al., "Diazotrophic endophytes: Progress and prospects for nitrogen fixation in monocots." Plant and Soil, (1996) 186:29-38 (Abstract).
European Patent Search Report (EP1036492A1).
PCT Search Report (PCT/US01/46524).
European Patent Search Report (EP 01 99 6114).

(Continued)

*Primary Examiner*—Irene Marx
(74) *Attorney, Agent, or Firm*—Dykema Gossett PLLC; Lisa V. Mueller; Gregory M. Zinkl

(57) ABSTRACT

A biological inoculant for enhancing the growth of plants is disclosed. The inoculant includes the bacterial strains *Herbaspirillum seropedicae* 2A, *Pantoea agglomerans* P101, *Pantoea agglomerans* P102, *Klebsiella pneumoniae* 342, *Klebsiella pneumoniae* zmvsy, *Herbaspirillum seropedicae* Z152, *Gluconacetobacter diazotrophicus* PA15, with or without a carrier. The inoculant also includes strains of the bacterium *Pantoea agglomerans* and *K. pneumoniae* which are able to enhance the growth of cereal grasses. Also disclosed are the novel bacterial strains *Herbaspirillum seropedicae* 2A, *Pantoea agglomerans* P101 and P102, and *Klebsiella pneumoniae* 342 and zmvsy.

2 Claims, No Drawings

OTHER PUBLICATIONS

P.J. Riggs et al, "Enhanced maize productivity by inoculation with diazotrophic bacteria" CSIRO publishing—Functional Plant Biology & 8th International Symposium on Nitrogen Fixation with Non-legumes, Dec. 3, 2000, Sydney, NSW, AU & Australian Journal of Plant Physiology, vol. 28, No. 9, 2001, pp. 829-836.

M.K. Chelius et al., "Immunolocalization of Dinitrogenase Reductase Produced by *Klebsiella pneumoniae* in Association with Zea mays L." Applied and Environmental Microbiology, vol. 66, No. 2., Feb. 2000, pp. 783-787.

M.E. Will et al., "Interaction of Rhizosphere Bacteria, Fertilizer, and Vesicular-Arbuscular Mycorrhizal Fungi with Sea Oats" Applied and Environmental Microbiology, vol. 56, No. 7, Jul. 1990, pp. 2073-2079.

Hassouna Mohammed Gamal et al., "Increased yields of alfalfa (*Medicago sativa*) inoculated with N-2-fixing bacteria and cultivated in a calcareous soil of northwestern Egypt" Biosciences Information Service, Philadelphia, PA US 1994 & Arid Soil Research and Rehabilitation, vol. 8, No. 4, 1994, pp. 389-393. (Abstract).

Sengupta B et al., "Nitrogen Fixation in the Phyllosphere of Tropical Plants Occurence of Phyllosphere Nitrogen Fixing Microorganisms in Eastern India and Their Utility for the Growth and Nitrogen Nutrition of Host Plants" Bioscience Information Service, Philadelphia, PA, US, 1981 and Annals of Botany (London) vol. 48, No. 5, 1981, pp. 705-716 (Abstract).

Nandi A. S. et al., "Utility of Phyllosphere Nitrogen Fixing Microorganisms in the Improvement of Growth of Some Vegetables" Biosciences Information Service, Philadelphia, PA, US, 1983, & Journal of Horticultural Science, vol. 58, No. 4, 1983, pp. 547-554. (Abstract).

Nandi A. S. et al., "Utility of Some Nitrogen Fixing Microorganisms in the Phyllosphere of Crop Plants" Biosciences Information Service, Philadelphia, PA, US, 1981 & Plant and Soil, vol. 63, No. 3, 1981, pp. 465-476 (Abstract).

Samanta R et al., "Further Observations on the Utility of Nitrogen-Fixing Microorganisms in the Phyllosphere of Cereals" Biosciences Information and Service, Philadelphia, PA, US 1986 & Journal of Agricultural Science, vol. 107, No. 3, 196, pp. 673-680 (Abstract).

Haahtela K et al., "Root-Associated Enterobacter and Klebsiella in POA-Pratensis Characterization of An Iron-Scavenging System and a Substance Stimulating Root Hair Production" Biosciences Information Service, Philadelphia, PA , US 1990 & Molecular Plant-Microbe Interactions, vol. 3, No. 6, 1990, pp. 358-365. (Abstract).

Derwent Publications Ltd., London, GB; Class A947, AN 1985-107708 Section Ch, Week 198518 & JP 60 051684A Mar. 23, 1985 (Abstract).

M. Chelius et al., "Diazotrophic Endophytes Associated with Maize", pp. 779-791 "Prokaryotic Nitrogen Fixation: A Model System for Analyses of a Biological Process" 2000, Horizon Scientific Press, Wymondham, UK.

El-Khawas H et al., "Identification and quantification of auxins in culture media of Azospirillum and Klebsiella and their effect on rice roots" Biosciences Information Service, Philadelphia, Pa, US & Biology and Fertility of Soils, vol. 28. No. 4, Feb. 1999, pp. 377-381. (Abstract).

Hassouma Mohammed Gama et al., "Biocontrol of soil-borne plant pathogens attacking cucumber (*Cucumis sativus*) by rhizobacteria in a semiarid environment" Biosciences Information Service Philadelphia, PA, US & Arid Soil Research and Rehabilitation, vol. 12, No. 4, Oct. 1998, pp. 345-357. (Abstract).

P.J. Riggs et al. "Isolation and characterization of diazotroophic endophytes from grasses and their effects on plant growth" Chemical Abstracts Service Columbus, Ohio, US & Nitrogen Fixation Global Perspectives, Proceedings of the International Congress on Nitrogen Fixation, 13th, Hamilton, on Canada, Jul. 2-7, 2001, pp. 263-267. (Abstract).

Dong Yuemei et al. "Genomic interspecies microarray hybridization: Rapid discovery of three thousand genes in the maize endophyte, *Klebsiella pneumoniae* 342, by microarray hybridization with *Escherichia coli* K-12 open reading frames" Biosciences Information Service Philadelphia, PA US Apr. 2001 & Applied and Environmental Microbiology, vol. 67, No. 4, Apr. 2001, pp. 1911-1921. (Abstract).

Riggs, P. J., et al., "Enhanced Maize and Wheat Productivity By Inoculation with Diazotrophic Endophytes", 8th International Symposium on Nitrogen Fixation with Non-Legumes, Sydney, AU (Dec. 3, 2000-Dec. 5, 2000).

European Patent Search Report (EP1036492 A1), date unavailable.

PCT Search Report (PCT/US01/46524), date unavailable.

European Patent Search Report (EP 01 99 6114), date unavailable.

Hassouna Mohammed Gamal et al., "Increased yields of alfalfa (*Medicago sativa*) inoculated with N-2-fixing bacteria and cultivated in a calcareous soil of northwestern Egypt" Biosciences Information Service, Philadelphia, PA US 1994 & Arid Soil Research and Rehabilitation, vol. 8, No. 4, 1994, pp. 389-393. (Abstract).

Ruppel, S. (1991) Serratia rubidea—an associative plant growth promoting nitrogen fixing microorganism. Zentralbl. Mikrobiol. 146:297-303.

* cited by examiner

KLEBSIELLA PNEUMONIAE INOCULANTS FOR ENHANCING PLANT GROWTH

CROSS-REFERENCE TO RELATED APPLICATIONS

This application is a divisional of U.S. application Ser. No. 10/005,412, filed on Dec. 3, 2001 now abandoned, which claims the benefit of U.S. Provisional Application No. 60/251,137 filed on Dec. 4, 2000.

STATEMENT REGARDING FEDERALLY SPONSORED RESEARCH OR DEVELOPMENT

The disclosed invention was made with United States government support awarded under contract DE-FC05-92OR22072 by the Unites States Department of Energy. The United States Government has certain right to this invention.

BACKGROUND OF THE INVENTION

Significant research has been conducted in recent years on the use of biological control agents to increase agricultural productivity and efficiency. These studies have shown that various microorganisms are able to suppress plant pathogens or supplement plant growth, thus offering an attractive alternative to chemical pesticides which are less favored because of their effect on human health and environmental quality.

Several screening programs have been used to isolate biological control agents effective in facilitating plant growth or combating pests in the laboratory or in the field. An example of one such biological control agent is *Bacillus thuringiensis*, which has been shown to produce toxic proteins lethal to certain insects. Another example is the bacterial strain *Bacillus cereus* UW85 (ATCC No. 53522), which has been found to protect alfalfa seedlings from damping off caused by *Phytophthora medicaginis*, tobacco seedlings from *Phytophthora nicotianae*, cucumber fruits from rot caused by *Phthium aphanidermatum*, and peanuts from Sclerotinia minor (See U.S. Pat. No. 4,877,738). In addition, *Bacillus cereus* AS4-12 (ATCC No. 55609) has been found to increase the efficacy in fostering the growth and establishment of alfalfa plants in the upper mid-western United States (See U.S. Pat. No. 5,552,138).

Earlier experiments have shown that strains of *Pantoea agglomerans* may also be able to increase the yield of legumes and inhibit the growth of phytopathogenic fungi. Hoflich and Ruppel, "Growth stimulation of pea after inoculation with associative bacteria," *Microbiol. Res.*, 149:99-104 (1994). *P. agglomerans* (formerly *Enterobacter agglomerans*) is a Gram-negative Enterobacterium often found associated with plants, water, soil, or foodstuffs. *P. agglomerans* is also a diazotroph, and able to fix nitrogen in both pure culture and in association with wheat. Merbach et al., "Dinitrogen fixation of microbe-plant associations as affected by nitrate and ammonium supply," *Isotopes Environ. Health Stud.*, 34:67-73 (1998). It has also been reported to produce two auxins and two cytokines in pure culture. Scholz et al., "Development of DAS-ELISA for some selected bacteria from the rhizosphere," *Zentralbl. Mikrobiol.* 146:197-207 (1991); Scholz-Seidel C. and Ruppel S., Nitrogenase and phytohormone activities of *Pantoea agglomerans* in Culture and their reflection in combination with wheat plants," *Zentralbl. Mikrobiol.* 147:319-328 (1992). Even with these studies, however, little is known about the interaction between *P. agglomerans* and cereal grasses, and whether *P. agglomerans* may serve as an effective biocontrol agent.

*Klebsiella pneumoniae* is also a member of the family Enterobacteriaceae and a known nitrogen fixing bacterium, i.e. able to convert atmospheric nitrogen into ammonium. *K. pneumoniae* is a free-living soil bacterium and unlike other nitrogen-fixing bacteria, such as Rhizobium, *K. pneumoniae* does not participate in symbiotic interactions with leguminous plants. *K. pneumoniae* has also not yet been shown to be effective in enhancing the growth of cereal grasses.

The mechanisms by which biological control agents are able to increase agricultural productivity and efficiency are diverse, and will vary depending upon the unique characteristics of each particular agent. It is believed, for example, that certain bacteria are able to control root rot in plants by competing with fungi for space on the surface of the plant root. It is also believed that competition between various bacterial strains in a plant's native microflora may stimulate root growth and increase the uptake of mineral nutrients and water to enhance plant yield. Alternatively, toxins produced by certain bacterial species are believed to facilitate plant growth by controlling bacterial species pathogenic to the plant. Bacterially produced antibiotics are an example of such toxins.

Some have suggested that bacterial strains other than those presently identified may also prove to be beneficial to crop plants. In particular, it is quite possible that some of these bacterial strains may be particularly helpful in cultivating various field crops as a result of relationships formed between plant and bacteria. The present invention discloses several such bacterial strains.

BRIEF SUMMARY OF THE INVENTION

The present invention is summarized as a method for enhancing the growth of a plant using an inoculum comprising an effective quantity of bacteria selected from the group consisting of *Klebsiella pneumoniae* 342, *Klebsiella pneumoniae* zmvsy, *Pantoea agglomerans* P101, *Pantoea agglomerans* P102, *Herbaspirillum seropedicae* 2A, *Herbaspirillum seropedicae* Z152, *Gluconacetobacter diazotrophicus* PA15, and any mutations thereof which retain the ability to enhance plant growth. The present invention also includes the bacterial inoculant of the above method, and a plant seed coated with the bacterial inoculant.

In addition, the present invention includes a method for identifying strains of *Pantoea agglomerans* and *Klebsiella pneumoniae* which have the ability to enhance the growth of cereal grasses. Also included is an inoculum comprising the bacterial strains identified by said method and a method for enhancing the growth of cereal grasses using said bacterial strains. The present invention also includes a plant seed coated with the inoculum.

The present invention is further characterized in that novel bacterial strains capable of enhancing the growth of a plant have been isolated from the environment. These strains include *Herbaspirillum seropedicae* 2A (ATCC No. PTA-2742), *Pantoea agglomerans* P101 (ATCC No. PTA 2744), *Pantoea agglomerans* P102 (ATCC No. PTA 2740), *Klebsiella pneumoniae* 342 (ATCC No. PTA-2743), *Klebsiella pneumoniae* zmvsy (ATCC No. PTA-2741), and mutations thereof which retain the ability to enhance the growth of plants.

It is an object of the present invention to provide a bacterial inoculant effective in facilitating the germination and/or growth of plants.

It is another object of the present invention to provide a biological agent capable of improving crop yield without additional chemical agents.

Other objects, advantages and features of the present invention will become apparent from the following specification when taken in conjunction with the accompanying claims.

BRIEF DESCRIPTION OF THE SEVERAL VIEWS OF THE DRAWINGS

None.

DETAILED DESCRIPTION OF THE INVENTION

The present invention is directed toward certain bacterial strains and inoculants capable of enhancing the growth of plants. The bacterial strains utilized in the present invention include *Herbaspirillum seropedicae* 2A, *Herbaspirillum seropedicae* Z152, *Pantoea agglomerans* P101, *Pantoea agglomerans* P102, *Klebsiella pneumoniae* 342, *Klebsiella pneumoniae* zmvsy, *Gluconacetobacter diazotrophicus* PA15, and any mutations thereof which retain the ability to enhance the growth of plants. Also included are strains of the bacterium *P. agglomerans* and *K. pneumoniae* which are able to enhance the growth of cereal grasses as identified by the method described below. As used herein, the above bacterial strains shall sometimes be referred to collectively as "enhancing" bacteria.

Bacterial strains *H. seropedicae* 2A, *P. agglomerans* P101, *P. agglomerans* P102, *K. pneumoniae* 342, and *K. pneumoniae* zmvsy are believed to be new to the world, and were deposited with the American Type Culture Collection ("ATCC"), Manassas, Va. 20110-2209 U.S.A., on Nov. 30, 2000. The bacterial strain *H. seropedicae* 2A was isolated from a maize plant cultivated in Hancock, Wis. during the summer of 1999, and has been given the ATCC Patent Deposit Designation PTA-2742. *P. agglomerans* P101 and *P. agglomerans* P102 were isolated from switch grass plants collected from a remnant prairie near Plover, Wis., and have been given the ATCC Patent Deposit Designation PTA 2744 and PTA 2740, respectively. *K. pneumoniae* 342 was isolated from a very nitrogen efficient line of maize from Mexico cultured in a greenhouse in Madison, Wis., and has been given the ATCC Patent Deposit Designation PTA-2743. *K. pneumoniae* zmvsy was isolated in 1994 from a maize plant grown on a farm in Madison, Wis., and has been given the ATCC Patent Deposit Designation PTA-2741.

Bacterial strains *H. seropedicae* Z152 (ATCC No. 35894) and *G. diazotrophicus* PA15 (ATCC No. 49037) were both previously known and available from the ATCC, but never shown to enhance the growth of cereal grasses. Both bacterial strains were isolated in the late 1980s from sugarcane in Brazil.

It is anticipated that certain mutants of the enhancing bacteria may also enhance plant growth comparable to the non-mutated forms set forth above. Mutants of the enhancing bacteria may include both naturally occurring and artificially induced mutants. Certain of these mutants will be found to enhance cereal grasses or legumes using the plant enhancement assay described below. Others mutants may be induced by subjecting the enhancing bacteria to known mutagens, such as N-methyl-nitrosoguanidine, using conventional methods. Similar mutants have been made from useful *Bacillus cereus* strains such as UW85 (ATCC No. 53522) and AS4-12 (ATCC No. 55609) as described in U.S. Pat. No. 4,877,738 and U.S. Pat. No. 5,552,138, respectively, the disclosure of which is hereby incorporated by reference.

The data set forth below in the Examples demonstrate that other strains of the bacterium *P. agglomerans* and *K. pneumoniae* will also be effective in enhancing the growth of cereal grasses when used in accordance with the present invention. These strains may be isolated using methods commonly known in the art for isolating free-living organisms from the environment, and their ability to enhance plant growth may be verified using any one of many plant enhancement assays.

The following is a disclosure of one such plant enhancement assay whereby a bacterial isolate, or the like, may be tested for its ability to enhance the growth of a cereal grass next to which it is placed. The seed or seedling of the cereal grass to be enhanced is planted in a planting medium and watered with a nutrient solution. The planting medium may be a damp soil, vermiculite in water, an agar-based formulation, or any other planting medium in which the seed or seedling will grow and develop. The bacterial isolate is placed at least in the immediate vicinity of the seed or seedling. Such placement shall be understood to be in the "immediate vicinity" of the seed or seedling if the bacterial isolate or any soluble exudate of a bacterium being tested will be in actual contact with the germinating seedling. After a time sufficient for seedling growth, seedlings developing from the planted seed may be evaluated for visual evidence of enhanced growth when compared to controls.

The bacterial inoculants of the present invention act through an unknown mechanism to enhance plant growth. While the mechanism by which these inoculants enhance plant growth is not understood, it is possible that the mechanism involves an antagonistic action by the enhancing bacterium on other organisms which may inhibit and/or retard the germination and growth of the plant seedling. The method of action may alternatively involve a symbiotic relationship of some unknown type.

It is broadly intended within the scope of the present invention that the bacterial inoculant of the present invention be inoculated into the soil with plant seeds so that a culture of the enhancing bacteria will develop in the root system of the plant as it grows. To facilitate this co-culturing, it is preferred that the inoculant, preferably diluted with a suitable extender or carrier, either be applied to the seeds prior to planting or introduced into the seed furrows when the seeds are planted. The bacterial inoculant so delivered may be any viable bacteria culture capable of successful propagation in the soil.

One advantageous technique is that the bacterial inoculant be applied to the seeds through the use of a suitable coating mechanism or binder prior to the seeds being sold into commerce for planting. The process of coating seed with such an inoculum is generally well known to those skilled in the art. For example, the enhancing bacteria may be mixed with a porous, chemically inert granular carrier as described by U.S. Pat. No. 4,875,921 (incorporated herein by reference).

Alternatively, the bacterial inoculant may be prepared with or without a carrier and sold as a separate inoculant to be inserted directly into the furrows into which the seed is planted. The process for inserting such inoculants directly into the furrows during seed planting is also generally well known in the art.

The enhancing bacteria may also be obtained in a substantially pure culture. A "substantially pure" culture shall be deemed to include a culture of bacteria containing no other bacterial species in quantities sufficient to interfere with the replication of the culture or be detected by normal bacteriological techniques.

Whether the bacterial inoculants are coated directly on the seed or inserted into the furrows, the enhancing bacteria is preferably diluted with a suitable carrier or extender so as to make the culture easier to handle and to provide a sufficient quantity of material so as allow easy human handling. For example, a peat based carrier may be used as described by Bosworth et al, "Alfalfa yield response to inoculation with recombinant strains of *Rhizobium meliloti* carrying an extra copy of dct and/or modified nifA expression," *Appl. Environ. Microbiol.*, 60:3815-3832 (1994), incorporated herein by reference. In addition, it has been discovered that perlite, vermiculite and charcoal materials are suitable carrier substances. It is believed that many other non-toxic and biologically inert substances of dried or granular nature are also capable of serving as carriers for the enhancing bacteria.

The density of inoculation of these bacterial cultures onto seed or into the furrows should be sufficient to populate the sub-soil region adjacent to the roots of the plant with viable bacterial growth. An effective amount of bacterial inoculant should be used. An effective amount is that amount sufficient to establish sufficient bacterial growth so that the yield from the plant is increased.

As stated above, the enhancing bacterial strains are isolated from the roots of exceptionally vigorous plants grown under conventional cultivation practices. Once isolation of the strains was made, the bacterial culture had to be cultivated to generate sufficient quantities of material for proper seed treatment. It has been discovered here that the inoculation of various cereal grasses with the enhancing bacterial strains results in significantly improved growth of the cereal grass plants. As will be appreciated by any person skilled in plant husbandry, the rate of growth or improvement in growth of any given crop is subject to many variables. It has been found here, however, that the co-cultivation of the bacterial inoculant of the present invention with cereal grasses is of significant advantage in at least some typical field conditions. It is believed that this co-cultivation technique will result generally in improved yield and improved growth of cereal grasses in field applications.

It is also anticipated that the inoculation of various legumes with the enhancing bacterial strains may result in significantly improved growth of legume plants.

It will be appreciated by one skilled in the art that a bacterial inoculant of the type described herein offers several significant potential advantages over the chemical inoculants or growth hormones or similar agents commonly used in agriculture today. By the very nature of the bacterial inoculant, the enhancing bacterial strains are self-sustaining in a continuous fashion once they are introduced into the furrows with the plant seed. Therefore, there is no need for retreatment of the plants during the crop season. The bacterium grows in cultivation along with the plants and should continue to exhibit its beneficial effect on the plant throughout the agricultural season. This is in strong contrast to chemical growth agents or fungicides which must be retreated periodically to have a continuing effect on inhibition of the fungus in question or to help improve the plant growth throughout its life cycle. Since the bacterial inoculant of the present invention can be inoculated onto the seeds using a dry or wet formulation, the application of this technique is relatively simple to the farmer since the seeds can be inoculated prior to distribution. In this way, a significant economic advantage is achievable.

The following non-limited examples are intended to illustrate the present invention.

EXAMPLES

Example 1

The bacterial strains which make up the bacterial inoculants of the present invention were isolated (or obtained from the ATCC in the case of *Gluconacetobacter diazotrophicus* PA15 and *Herbaspirillum seropedicae* Z152) and grown in culture on petri dishes at 28° C. to create crop inoculating propagules. The culturing media used for *Klebsiella pneumoniae* 342, *Klebsiella pneumoniae* zmvsy, *Pantoea agglomerans* P101 and *Pantoea agglomerans* P102 was Luria-Bertani medium. The medium used for *Gluconacetobacter diazotrophicus* PA15 was AcD medium, which contains per liter: 0.64 g $K_2HPO_4$, 0.16 g $KH_2PO_4$, 0.2 g $MgSO_47H_2O$, 0.2 g NaCl, 0.05 g $CaSO_4.2H_2O$, 20 g sucrose, 2 mg $NaMoO_4$, 3 mg $FeSO_4$, 2 g MES buffer, 1 g malic acid, and 0.1 g yeast extract. This medium was adjusted to pH 6.5 prior to autoclaving. Bacterial strains *Herbaspirillum seropedicae* 2A and *Herbaspirillum seropedicae* Z152 were cultured on BSM medium as described by Bergersen et al., "The Growth of *Rhizobium* in Synthetic Medium," *Aust. J. Biol. Sci.*, 14:349-360 (1961). All media contained 15 g/L of agar.

Wheat seeds from three cultivars (Trenton, Russ, and Stoa) were inoculated with the bacterial propagules to determine each bacterial strains' ability to affect plant growth. Seeds were first surface sterilized using 70% ethanol for 30 seconds and 10% bleach for 2 minutes, followed by 6 washes with sterile water. A cell suspension of approximately $10^8$ cells/ml was then added to the seeds for a few hours prior to planting to inoculate the wheat seeds.

Inoculated and uninoculated wheat seeds were planted approximately 1 cm deep in pots containing 2 liters of a 1:1 sand/vermicullite mixture. Plants were watered with a nutrient solution described by Chelius et al., "Immunolocalization of dinitrogenase reductase produced by *Klebsiella pneumoniae* in association with *Zea mays L.*," *Appl. Environ. Microbiol.*, 66:783-787 (2000), containing all essential nutrients except nitrogen. Four seeds were planted per pot which were thinned to two plants per pot after two weeks.

After six weeks of growth, the above ground portions of the plants were harvested, placed in a paper bag, and dried for one week in driers at about 80° C. After drying, the plants were weighed. The values shown in Table 1 below were obtained by comparing the average dry weight of the treated plants to the average dry weight of untreated plants.

TABLE 1

Changes in Dry-Shoot Weight of Wheat by Inoculation with Bacterial Inoculants

| Wheat Cultivar | Bacterial Inoculant | Ave. Dry Weight (mg/plant) | Dry Weight Difference |
|---|---|---|---|
| Trenton | Uninoculated | .257 | — |
|  | K. pneumoniae 342 | .789 | .532 |
|  | K. pneumoniae zmvsy | .500 | .243 |
|  | H. seropedicae 152 | .455 | .198 |
|  | H. seropedicae 2A | .440 | .183 |
|  | P. agglomerans 101 | .747 | .490 |
|  | P. agglomerans 102 | .601 | .344 |
|  | G. diazotrophicus PA15 | .382 | .125 |
| Russ | Uninoculated | .402 | — |
|  | K. pneumoniae 342 | .416 | .014 |

TABLE 1-continued

Changes in Dry-Shoot Weight of Wheat by
Inoculation with Bacterial Inoculants

| Wheat Cultivar | Bacterial Inoculant | Ave. Dry Weight (mg/plant) | Dry Weight Difference |
|---|---|---|---|
| | K. pneumoniae zmvsy | .467 | .065 |
| | H. seropedicae 152 | .400 | −.002 |
| | H. seropedicae 2A | .454 | .052 |
| | P. agglomerans 101 | .545 | .143 |
| | P. agglomerans 102 | .672 | .270 |
| | G. diazotrophicus PA15 | .392 | −.010 |
| Stoa | Uninoculated | .269 | — |
| | K. pneumoniae 342 | .380 | .111 |
| | K. pneumoniae zmvsy | .253 | −.016 |
| | H. seropedicae 152 | .336 | .067 |
| | H. seropedicae 2A | .213 | −.056 |
| | P. agglomerans 101 | .429 | .160 |
| | P. agglomerans 102 | .472 | .203 |
| | G. diazotrophicus PA15 | .299 | .030 |

Example 2

Field tests of corn were performed at the University of Wisconsin Hancock Agricultural Research Station (Hancock, Wis.) in which maize seeds of different varieties were inoculated with bacterial inoculants of the present invention.

The bacterial strains used were isolated (or obtained from the ATCC in the case of *Gluconacetobacter diazotrophicus* PA15 and *Herbaspirillum seropedicae* Z152) and grown in culture on petri dishes at 28° C. to create crop inoculating propagules. Most strains were cultured on Bergersen's synthetic medium (Bergersen F. J., "The growth of Rhizobium in synthetic media," *Aust. J. Biol. Sci.*, 14:349-360 (1961)). Bacterial strains *Klebsiella pneumoniae* 342 and *Klebsiella pneumoniae* zmvsy were cultured on Luria-Bertani medium (Sambrook et al., "Molecular cloning: a laboratory manual," (Cold Spring Harbor Laboratory Press: Cold Spring Harbor, N.Y., 1989)). *Gluconacetobacter diazotrophicus* PA15 was cultured on AcD medium (Burris R. H., "Comparative study of the response of *Azotobacter vinelandii* and *Acetobacter diazotrophicus* to changes in pH," *Protoplasma*, 183:62-66 (1994)).

Maize seeds were inoculated prior to planting by coating 1 kg of seeds with a 125 mL bacterial suspension in 8 grams of peat (0.566 g $CaCO_3$, 0.288 g charcoal, 10 mL 40% Vitalive (Research Seeds Inc., St. Joseph, Mo., USA) in a plastic bag. The cell suspension contained approximately $8 \times 10^8$ cells per mL to ensure an inoculum density of $10^8$ cells per seed. Cell number per seed was verified after inoculation by suspending seeds in water and plating various dilutions on the appropriate medium. The seeds included seeds from maize inbred lines B73 and Mo17; the hybrid B73×Mo17; two lines with a significant teosinte background, ¼ teosinte background, and ½ teosinte background; and various hybrid lines from Pioneer.

Seeds were planted within 48 hours of inoculation in rows thirty feet in length, with 30 seeds planted per row. Rows were approximately 36 inches apart. Weeds were controlled chemically by standard agricultural practices for the region. Fertilizer was applied prior to planting at rates of 17.2 g m$^{-2}$ $P_2O_5$ and 51.5 g m$^{-2}$ $K_2O$. Where nitrogen was applied, it was applied at a rate of 224 kg $NH_4NO_3$ ha$^{-1}$ prior to planting. An uninoculated control was included with each maize line.

After the growing season, the treated corn was harvested and grain weight and moisture-measured for each plot. Yield was determined as grain yield in t ha$^{-1}$, standardized to 15.5% moisture. Grain was harvested with a combine equipped with a HarvestMaster data logger (HarvestMaster, Inc., Logan, Utah, USA) for the determination of weight and moisture levels of the grain from each plot. The values shown in Table 2 below illustrate the increased yield per acre (or hectare), after correcting for moisture levels. Grain yield is expressed in metric t ha$^{-1}$. Only those combinations where statistically significant increases were obtained are listed.

TABLE 2

Yield Increase of Corn by Inoculation with Bacterial Inoculants

| Year | Corn Variety | Bacterial Inoculant | N (+/−) | Yield (t ha$^{-1}$) | % Yield Increase |
|---|---|---|---|---|---|
| 1998 | Pioneer 3905 | H. Seropedicae Z152 | + | 10.6 | 12.0 |
| | Pioneer 3905 | G. diazotrophicus PA15 | + | 9.96 | 5.4 |
| | Pioneer 3905 | K. pneumoniae zmvsy | + | 10.8 | 13.9 |
| | B73 x Mo17 | H. Seropedicae Z152 | + | 8.67 | 14.4 |
| | B73 x Mo17 | G. diazotrophicus PA15 | + | 9.50 | 25.3 |
| | B73 x Mo17 | K. pneumoniae zmvsy | + | 8.40 | 10.7 |
| | 1/2 teosinte | H. Seropedicae Z152 | + | 6.04 | 10.4 |
| | 1/2 teosinte | K. pneumoniae zmvsy | + | 6.31 | 15.3 |
| | Pioneer 3921 | G. diazotrophicus PA15 | − | 5.8 | 18.1 |
| 1999 | Pioneer 3751 | H. Seropedicae Z152 | + | 7.81 | 13.4 |
| | Pioneer 3751 | K. pneumoniae zmvsy | + | 8.2 | 18.7 |
| | Pioneer 36H36 | H. Seropedicae Z152 | + | 7.17 | 8.0 |
| | Pioneer 36H36 | K. pneumoniae zmvsy | + | 6.64 | 10.6 |
| | Pioneer 3921 | H. Seropedicae Z152 | − | 2.88 | 18.2 |
| | Pioneer 3921 | G. diazotrophicus PA15 | − | 5.08 | 18.1 |
| | Pioneer 3921 | P. agglomerans P101 | − | 2.6 | 13.1 |
| | Pioneer 3921 | P. agglomerans P103 | − | 2.96 | 30.1 |
| | Pioneer 3905 | K. pneumoniae 342 | − | 3.14 | 22.0 |
| | B73 x Mo17 | P. agglomerans P102 | − | 1.53 | 19.9 |

Example 3

Additional field tests were performed at the University of Wisconsin Arlington Agricultural Research Station (Arlington, Wis.) in a manner similar to Example 2. After the growing season, the treated corn was harvested and grain weight and moisture measured for each plot. The values shown in Table 3 below illustrate the increased yield per acre (or hectare), after correcting for moisture levels. Grain yield is expressed in metric t ha$^{-1}$. Only those combinations where statistically significant increases were obtained are listed.

TABLE 3

Yield Increase of Corn by Inoculation with Bacterial Inoculants

| Year | Corn Variety | Bacterial Inoculant | N (+/−) | Yield (t ha$^{-1}$) | % Yield Increase |
|---|---|---|---|---|---|
| 1998 | Pioneer 3905 | H. Seropedicae Z152 | + | 8.96 | 19.5 |
| | Pioneer 3921 | H. Seropedicae Z152 | + | 8.75 | 8.5 |
| | 1/2 teosinte | H. Seropedicae Z152 | + | 4.46 | 8.3 |
| 1999 | Pioneer 36H36 | H. Seropedicae Z152 | + | 7.66 | 18.8 |
| | Pioneer 36H36 | G. diazotrophicus PA15 | + | 7.88 | 23.4 |
| | Pioneer 36H36 | K. pneumoniae zmvsy | + | 7.58 | 18.6 |
| | Pioneer 3921 | H. Seropedicae Z152 | + | 6.77 | 13.2 |
| | Pioneer 3921 | K. pneumoniae zmvsy | + | 6.72 | 7.3 |
| | Pioneer 3905 | H. Seropedicae Z152 | + | 6.78 | 12.6 |
| | Pioneer 3905 | G. diazotrophicus PA15 | + | 6.92 | 14.4 |
| | Pioneer 3905 | K. pneumoniae 342 | + | 6.68 | 30.5 |
| | Pioneer 3905 | P. agglomerans P103 | + | 6.04 | 18.0 |
| | Pioneer S1501 | H. Seropedicae Z152 | + | 7.55 | 17.5 |
| | B73 x Mo17 | P. agglomerans P103 | + | 6.27 | 9.4 |
| 2000 | Pioneer 36H36 | H. Seropedicae Z152 | + | 15.51 | 7.3 |
| | Pioneer 36H36 | P. agglomerans P103 | + | 13.56 | 17.8 |
| | Pioneer 3921 | K. pneumoniae zmvsy | + | 15.9 | 20.0 |
| | Pioneer 3921 | H. Seropedicae Z152 | + | 14.86 | 12.1 |

Example 4

Additional field tests were performed at the University of Wisconsin Lancaster Agricultural Research Station (Lancaster, Wis.) in a manner similar to Examples 2 and 3. Plots in four other states, Iowa, Indiana, Illinois and Nebraska were established with the same design. All tests included the application of nitrogen as described above. After the growing season, the treated corn was harvested and grain weight and moisture measured for each plot. The values shown in Table 4 below illustrate the increased yield per acre (or hectare), after correcting for moisture levels. Grain yield is expressed in metric t ha$^{-1}$. Only those combinations where statistically significant increases were obtained are listed.

TABLE 4

Yield Increase of Corn by Inoculation with Bacterial Inoculants

| Year | Corn Variety | Bacterial Inoculant | Location | Yield (t ha$^{-1}$) | % Yield Increase |
|---|---|---|---|---|---|
| 2000 | Pioneer 36H36 | K. pneumoniae 342 | Lancaster | 16.39 | 25.8 |
| | Pioneer 36H36 | H. Seropedicae Z152 | Iowa | 8.89 | 10.7 |
| | Pioneer 36H36 | H. Seropedicae Z152 | Nebraska | 9.77 | 1.8 |
| | Pioneer 36H36 | H. Seropedicae Z152 | Illinois | 11.07 | 6.4 |
| | Pioneer 36H36 | G. diazotrophicus PA15 | Iowa | 9.25 | 15.2 |
| | Pioneer 36H36 | G. diazotrophicus PA15 | Nebraska | 9.83 | 2.4 |
| | Pioneer 36H36 | G. diazotrophicus PA15 | Illinois | 11.18 | 7.4 |
| | Pioneer 36H36 | G. diazotrophicus PA15 | Indiana | 8.4 | 8.1 |
| | Pioneer 36H36 | P. agglomerans P103 | Iowa | 8.94 | 11.3 |
| | Pioneer 36H36 | P. agglomerans P103 | Illinois | 10.74 | 3.2 |
| | Pioneer 33A14 | H. Seropedicae Z152 | Iowa | 10.77 | 1.6 |
| | Pioneer 33A14 | H. Seropedicae Z152 | Nebraska | 10.24 | 4.7 |
| | Pioneer 33A14 | H. Seropedicae Z152 | Illinois | 12.82 | 19.6 |
| | Pioneer 33A14 | H. Seropedicae Z152 | Indiana | 10.03 | 8.1 |
| | Pioneer 33A14 | G. diazotrophicus PA15 | Iowa | 11.09 | 1.6 |
| | Pioneer 33A14 | G. diazotrophicus PA15 | Nebraska | 9.88 | 1.0 |
| | Pioneer 33A14 | G. diazotrophicus PA15 | Illinois | 12.46 | 16.2 |
| | Pioneer 33A14 | G. diazotrophicus PA15 | Indiana | 9.41 | 1.4 |
| | Pioneer 33A14 | P. agglomerans P103 | Nebraska | 10.17 | 4.0 |
| | Pioneer 33A14 | P. agglomerans P103 | Illinois | 12.63 | 17.8 |
| | Pioneer 33A14 | P. agglomerans P103 | Indiana | 10.60 | 14.2 |

Example 5

Rice seeds were inoculated with the bacterial inoculants as described in Example 1 above to determine each bacterial strains' ability to affect the growth of rice plants. Seeds were first surface sterilized using 70% ethanol for 30 seconds and 10% bleach for 2 minutes, followed by 6 washes with sterile water. A cell suspension of approximately 10$^8$ cells/ml was then added to the seeds to inoculate the seeds for a few hours prior to planting.

Inoculated and uninoculated rice seeds were planted approximately 1 cm deep in pots containing 2 liters of a 1:1 sand/vermicullite mixture. Plants were watered with a nutrient solution described by Chelius et al., "Immunolocalization of dinitrogenase reductase produced by Klebsiella pneumoniae in association with Zea mays L.," Appl. Environ. Microbiol., 66:783-787 (2000), containing all essential nutrients except nitrogen. Four seeds were planted per pot which were thinned to two plants per pot after two weeks.

After six weeks of growth, the rice shoots of the plants were harvested, placed in a paper bag, and dried for one week in driers at about 80° C. After drying, the plants were weighed. The values shown in Table 5 below were obtained by comparing the average dry weight of the treated plants to the average dry weight of untreated plants.

TABLE 5

Changes in Dry-Shoot Weight of Rice by Inoculation with Bacterial Inoculants

| Bacterial Inoculant | Ave. Dry Weight (mg/plant) | Dry Weight Difference |
|---|---|---|
| Uninoculated | 240.4 | — |
| K. pneumoniae 342 | 247.4 | 7.0 |
| P. agglomerans 101 | 376.5 | 136.1 |

TABLE 5-continued

Changes in Dry-Shoot Weight of Rice by Inoculation with Bacterial Inoculants

| Bacterial Inoculant | Ave. Dry Weight (mg/plant) | Dry Weight Difference |
|---|---|---|
| P. agglomerans 102 | 273.3 | 32.9 |
| G. diazotrophicus PA15 | 248.2 | 7.8 |

We claim:

1. An inoculum for application to plants, said inoculum comprising a carrier and an effective quantity of a biologically pure bacterial culture of bacteria, wherein the bacteria are selected from Klebsiella pneumoniae 342 (ATCC No. PTA-2743), and Klebsiella pneumoniae zmvsy (ATCC No. PTA-2741), and further wherein an effective quantity of a biologically pure bacterial culture is a quantity sufficient to enhance the growth of wheat, rice or corn.

2. A biologically pure bacterial culture wherein the bacteria is selected from Klebsiella pneumoniae 342 (ATCC No. PTA-2743) and Klebsiella pneumoniae zmvsy (ATCC No. PTA-2741).

* * * * *